(12) United States Patent
Compton

(10) Patent No.: US 10,107,936 B2
(45) Date of Patent: Oct. 23, 2018

(54) ATOMIC INTERFEROMETRIC ACCELEROMETER WITH ENHANCED VIBRATIONAL STABILITY

(71) Applicant: Honeywell International Inc., Morris Plains, NJ (US)

(72) Inventor: Robert Compton, Loretto, MN (US)

(73) Assignee: Honeywell International Inc., Morris Plains, NJ (US)

( * ) Notice: Subject to any disclaimer, the term of this patent is extended or adjusted under 35 U.S.C. 154(b) by 201 days.

(21) Appl. No.: 15/138,035

(22) Filed: Apr. 25, 2016

(65) Prior Publication Data

US 2017/0307652 A1     Oct. 26, 2017

(51) Int. Cl.
| | | |
|---|---|---|
| *G01V 7/00* | (2006.01) | |
| *G01V 7/02* | (2006.01) | |
| *G01B 9/02* | (2006.01) | |
| *G01P 15/08* | (2006.01) | |
| *G01P 15/093* | (2006.01) | |
| *G01N 21/64* | (2006.01) | |

(52) U.S. Cl.
CPC .......... *G01V 7/00* (2013.01); *G01B 9/02003* (2013.01); *G01B 9/02045* (2013.01); *G01P 15/0802* (2013.01); *G01P 15/093* (2013.01); *G01V 7/02* (2013.01); *G01B 2290/25* (2013.01); *G01B 2290/70* (2013.01); *G01N 21/64* (2013.01)

(58) Field of Classification Search
CPC ......... G01B 9/02003; G01V 7/00; G01V 7/02
USPC ............................................ 73/382 R, 382 G
See application file for complete search history.

(56) References Cited

U.S. PATENT DOCUMENTS

| | | | |
|---|---|---|---|
| 4,874,942 A | 10/1989 | Clauser | |
| 4,992,656 A | 2/1991 | Clauser | |
| 5,274,231 A | 12/1993 | Chu et al. | |
| 5,698,847 A * | 12/1997 | Yoda ........................ | G01D 5/26 250/225 |

(Continued)

OTHER PUBLICATIONS

European Patent Office, "Extended European Search for EP Application No. 17163450.4", Foreign Counterpart to U.S. Appl. No. 15/138,035, dated Sep. 7, 2017, pp. 1-9, Published in: EP.

(Continued)

*Primary Examiner* — Lisa Caputo
*Assistant Examiner* — Herbert K Roberts
(74) *Attorney, Agent, or Firm* — Fogg & Powers LLC

(57) ABSTRACT

An atomic interferometric accelerometer comprises a laser that emits a pulsed beam at a first frequency, an electro-optic modulator that receives the beam, and a vacuum cell in communication with the electro-optic modulator. The electro-optic modulator outputs a first optical signal corresponding to the beam at the first frequency and a second optical signal having a second frequency different from the first frequency. The vacuum cell has a chamber for laser cooled atoms. The vacuum cell receives the optical signals such that they propagate in a direction that passes through the atoms. A piezo mirror retro-reflects the optical signals back through the vacuum cell in a counter-propagating direction. The piezo mirror is driven with substantially constant velocity during a beam pulse, thereby imparting a Doppler shift to the retro-reflected optical signals to create two non-symmetric counter-propagating lightwave pairs. One of the lightwave pairs supports interferometry while the other is non-resonant.

20 Claims, 3 Drawing Sheets

(56) References Cited

U.S. PATENT DOCUMENTS

| | | | |
|---|---|---|---|
| 6,181,429 B1* | 1/2001 | Barberis | G01N 21/45 356/477 |
| 9,018,579 B2 | 4/2015 | Kasevich et al. | |
| 9,291,508 B1 | 3/2016 | Biedermann et al. | |
| 2006/0232783 A1* | 10/2006 | Choma | G01B 9/02004 356/479 |
| 2013/0169973 A1* | 7/2013 | Inoue | G01B 9/02091 356/497 |
| 2014/0190254 A1 | 7/2014 | Bouyer et al. | |
| 2014/0375998 A1 | 12/2014 | Kasevich et al. | |

OTHER PUBLICATIONS

Sengstock et al., "Optical Ramsey Spectroscopy on Laser-Trapped and Thermal Mg Atoms", Applied Physics B: Lasers and Optics, Aug. 1, 1994, pp. 99-115, vol. B59, No. 2, Publisher: Springer International, Published in: Berlin, DE.

Hamilton et al., "Concept of a miniature atomic sensor", 2014 International Symposium on Inertial Sensors and Systems (ISISS), Feb. 25, 2014, pp. 1-4.

Kasevich et al., "Measurement of the Gravitational Acceleration of an Atom with a Light-Pulse Atom Interferometer", Applied Physics B, May 1992, pp. 321-332, vol. 54, No. 5.

* cited by examiner

ATOMIC INTERFEROMETRIC ACCELEROMETER WITH ENHANCED VIBRATIONAL STABILITY

BACKGROUND

Atomic interferometric accelerometers use two counter-propagating lightwaves with differing frequency to divide and recombine atomic waves, and to read out their phase shifts due to inertial forces. In a large lab-scale system, these lightwaves can be directed via mirrors through opposing windows of a vacuum chamber that contains the atomic waves. This beam-path adds significant additional size, weight, and cost to the system, as well as increasing sensitivity to vibrations. A proven practice is to introduce both lightwaves through the same window, and then retro-reflect them both from a mirror in order to generate the necessary counter-propagating beams, as this approach also reduces interferometer phase noise. Unfortunately, this approach by itself creates two competing interferometers formed by the two sets of counter-propagating lightwaves or beam pairs. Thus, it is necessary to select only one of the two beam pairs in order to avoid competition between the two beam pairs that would degrade bias and scale factor (SF) stability.

In order to select only one pair of laser beams, a technique has been demonstrated in lab-scale systems in which velocity is imparted to the atom waves prior to initiating the interferometer cycle. This additional velocity induces a Doppler shift in the atom/light interaction, and breaks the symmetry between left-going and right-going lightwaves, making it possible to tune the laser frequencies such that only one pair of lightwaves is resonant with the atoms. However, this technique is difficult to implement in a small or miniature atomic interferometric accelerometer, since it requires additional lasers and because the imparted velocity reduces the time available for interrogation of the atoms.

SUMMARY

An atomic interferometric accelerometer comprises a laser device configured to emit a pulsed laser beam at a first frequency, an electro-optic modulator in optical communication with the laser device and configured to receive the pulsed laser beam at the first frequency, and a vacuum cell in optical communication with the electro-optic modulator. The electro-optic modulator is configured to output a first optical signal corresponding to the pulsed laser beam at the first frequency and a second optical signal having a second frequency different from the first frequency. The vacuum cell comprises a plurality of optically transparent sides that enclose a vacuum chamber in which laser cooled atoms reside. The vacuum cell is configured to receive the first and second optical signals such that the first and second optical signals propagate in a direction that passes through the laser cooled atoms. A piezo mirror structure is in optical communication with the vacuum cell and is configured to retro-reflect the first and second optical signals back through the laser cooled atoms in a counter-propagating direction. The piezo mirror structure is driven with substantially constant velocity during each individual laser beam pulse, thereby imparting a Doppler shift to the retro-reflected first and second optical signals to create two non-symmetric counter-propagating lightwave pairs. One of the lightwave pairs supports interferometry while the other of the lightwave pairs is non-resonant.

BRIEF DESCRIPTION OF THE DRAWINGS

Features of the present invention will become apparent to those skilled in the art from the following description with reference to the drawings. Understanding that the drawings depict only typical embodiments and are not therefore to be considered limiting in scope, the invention will be described with additional specificity and detail through the use of the accompanying drawings, in which.

DETAILED DESCRIPTION

In the following detailed description, embodiments are described in sufficient detail to enable those skilled in the art to practice the invention. It is to be understood that other embodiments may be utilized without departing from the scope of the invention. The following detailed description is, therefore, not to be taken in a limiting sense.

An atomic interferometric accelerometer with improved vibrational stability is provided. The atomic interferometric accelerometer is configured such that two lightwaves (laser beams) are directed into a miniature vacuum cell, which contains alkali atoms. The lightwaves pass through the vacuum cell, are retro-reflected by a piezo mounted mirror, and then return back through the vacuum cell in a counter-propagating fashion. The piezo mounted mirror is driven with a substantially constant velocity throughout the duration of each laser pulse, thereby imparting a Doppler shift to the retro-reflected lightwaves. This Doppler shift breaks the symmetry between forward-traveling and back-reflected lightwaves, enabling a setup in which only one pair of lightwaves supports interferometry, while the other pair is non-resonant.

In one embodiment, the piezo mounted mirror is driven by a sawtooth waveform that has a substantially constant velocity throughout the duration of each laser pulse. The sawtooth waveform resets the position of the piezo mounted mirror after each individual laser pulse, which can be about 1-100 µs is in duration.

The piezo velocity can be fixed with high precision and stability. For example, a portion of the back-reflected light is interfered with the forward-traveling light to produce a beat note, which is detected and used to give a measure of the piezo velocity. The beat note can be combined with a reference RF signal to feed-back an error signal to a controller coupled to the piezo mounted mirror.

The present approach provides for a much smaller and vibration insensitive design for the accelerometer, while maintaining higher performance at a lower cost and increasing robustness.

Further details of the present system and method are described hereafter with reference to the drawings.

Figure 1:
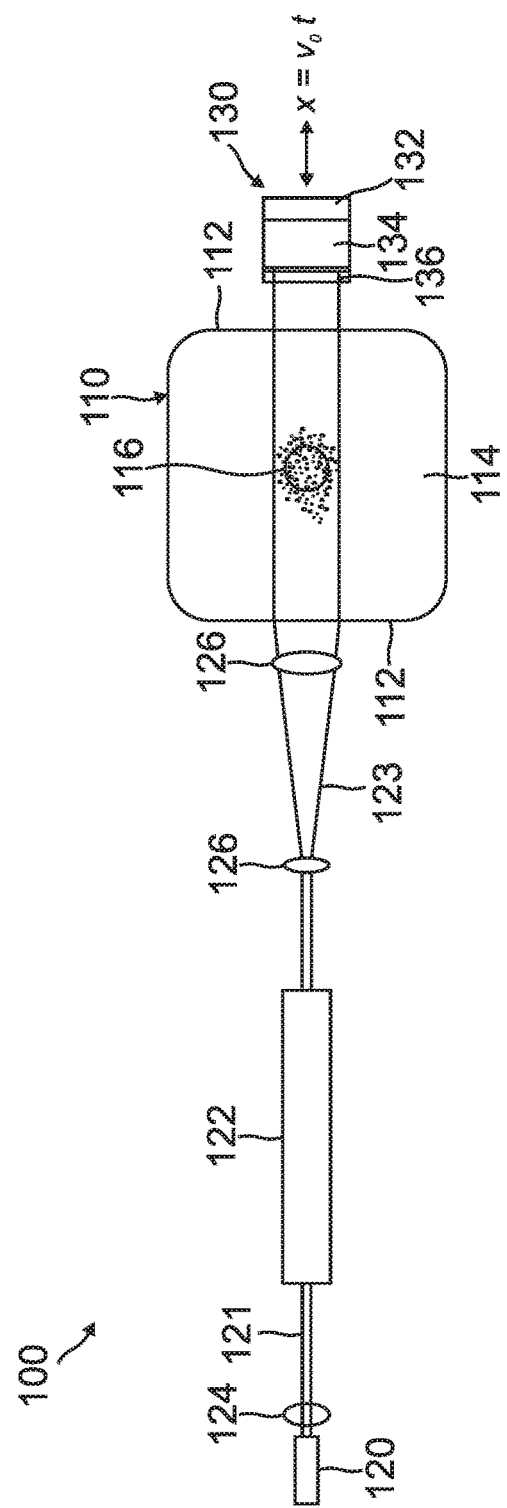
FIG. 1 is a block diagram of an atomic interferometric accelerometer with enhanced vibrational stability according to one embodiment.

FIG. 1 illustrates an atomic interferometric accelerometer 100 with enhanced vibrational stability, according to one embodiment. The atomic interferometric accelerometer 100 generally includes a vacuum cell 110 in optical communication with a laser device 120 through various optical components, and a movable piezo mirror structure 130 in optical communication with vacuum cell 110.

The vacuum cell 110 has optically transparent sides 112, which enclose a vacuum chamber 114 filled with laser cooled atoms 116, such as rubidium, cesium, or other alkali atoms. The atoms 116 can be laser cooled using conventional orthogonal laser beam paths that are directed into vacuum chamber 114. Such orthogonal laser beam paths are not shown in FIG. 1 for simplicity, but one of the orthogonal beam paths can be the same as a Raman beam path 123 as depicted.

The laser device 120 can be a laser diode, such as a distributed Bragg reflector (DBR) laser. An electro-optic modulator 122 is configured to receive a pulsed laser beam 121 emitted by laser device 120, with laser beam 121 having a first frequency $f_0$. The pulsed laser beam 121 can be passed through a first collimator 124 prior to entering electro-optic modulator 122, with first collimator 124 located in a first optical path between laser device 120 and electro-optic modulator 122. The electro-optic modulator 122 outputs a first optical signal corresponding to the pulsed laser beam at the first frequency ($f_0$) and a second optical signal having a second frequency ($f_0 + f_{RF}$). The first and second optical signals are sent through a second collimator 126 to vacuum cell 110 along Raman beam path 123. The second collimator 126 is located in a second optical path between electro-optic modulator 122 and vacuum cell 110. The first and second collimators 124, 126 can be single lens or multi-lens collimators.

The movable piezo mirror structure 130 is located outside of vacuum cell 110 on an opposite side from second collimator 126. In one embodiment, piezo mirror structure 130 includes a piezoelectric element 132, a mirror element 134 on the piezoelectric element 132, and a quarter-waveplate 136 on mirror element 134. The piezoelectric element 132 provides a sawtooth displacement with a velocity $v_0$ yielding a Doppler shift $f_D = f_0 v_0/c$, with c being the speed of light.

During operation, two forward propagating lightwaves having the respective frequencies of $f_0$ and $f_0 + f_{RF}$ are directed into vacuum cell 110, pass through laser cooled atoms 116, and pass out of vacuum cell 110. These lightwaves are retro-reflected by mirror element 134, and then return back through vacuum cell 110 in a counter-propagating fashion as back-reflected lightwaves having respective frequencies of $f_0 - f_D$ and $f_0 + f_{RF} - f_D$.

While piezoelectric elements typically have a very short range of travel, only a range of about 10 microns over a timescale of about 100 μs is needed to break the symmetry between the competing interferometers in atomic interferometric accelerometer 100. The piezoelectric element 132 can then reset to its initial position and await the next laser beam pulse.

The piezo mirror structure 130 introduces a Doppler shift between the laser beam and the atoms, as if the atoms had actually been launched. But the piezo mirror structure 130 only has to be moving when the laser beam is being pulsed so it only travels a total distance (x) of microns rather than millimeters, according to the following equation:

$$x = v_0 t$$

where x is the total distance, and t is the laser beam pulse time. For example, a velocity of 1 m/s at a pulse time of 100 μs, would result in a travel distance of 100 μm.

In the present approach, it is desirable that a selected pair of counter-propagating lightwaves have a frequency difference $f_{HF}$ equal to the atomic hyperfine (HF) splitting for the atomic species in question. For example, if the atoms are rubidium, the $f_{HF}$=6.8 GHz.

The incident laser source contains frequencies $f_0$ and $f_0 + f_{RF}$, where the radio-frequency (RF) offset is given by $f_{RF} = f_{HF} + f_D$, and the additional frequency shift $f_D$ is chosen to be equal to the Doppler shift induced by the motion of the piezoelectric element. The RF frequency shift is written onto both the incident and retro-reflected lightwaves, but the motion induced Doppler shift applies only to the retro-reflected beam.

The possible pairs of incident and retro-reflected beams are as follows. Incident $f_0$ combined with the motionally Doppler shifted $f_0 + f_{RF} - f_D = f_0 + f_{HF}$. This beam pair has a total frequency difference $f_{HF}$ and therefore supports atomic interferometry. Incident $f_0 + f_{RF} = f_0 + f_{HF} + f_D$ combined with motionally Doppler shifted $f_0 - f_D$. This beam pair has total frequency difference $f_{HF} + 2f_D$ and therefore does not support atomic interferometry. Either incident $f_0$ or incident $f_0 + f_{RF}$ combined with either of their retro-reflected selves do not support atomic interferometry, since $f_D \ll f_{RF}$.

Figure 2:
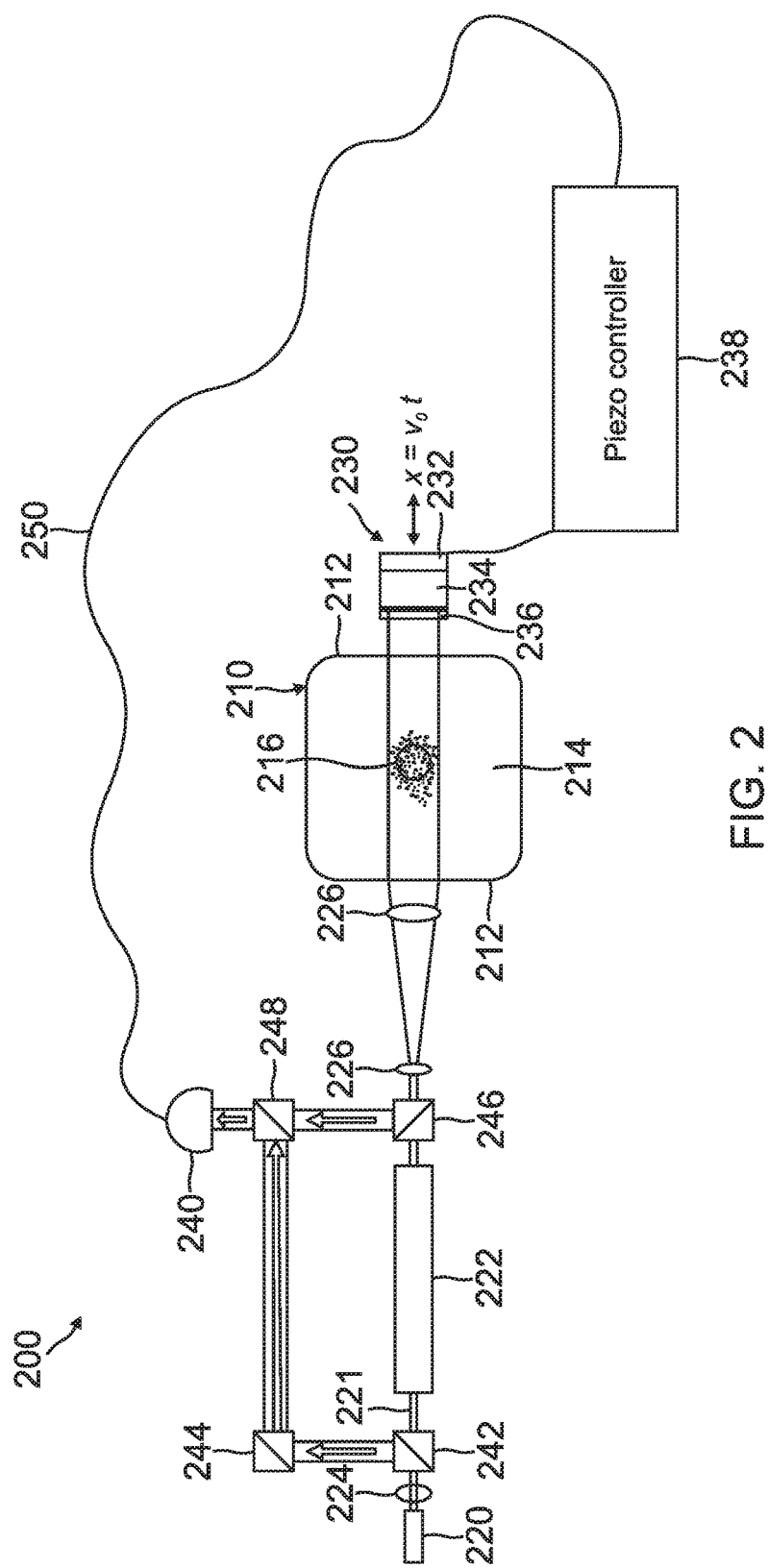
FIG. 2 is a block diagram of an atomic interferometric accelerometer with enhanced vibrational stability according to another embodiment.

FIG. 2 illustrates an atomic interferometric accelerometer 200 with enhanced vibrational stability, according to another embodiment. The atomic interferometric accelerometer 200 generally includes a vacuum cell 210 in optical communication with a laser device 220 through various optical components, and a movable piezo mirror structure 230 in optical communication with vacuum cell 210.

The vacuum cell 210 has optically transparent sides 212, which enclose a vacuum chamber 214 filled with laser cooled atoms 216. The atoms 216 can be laser cooled using conventional orthogonal laser beam paths that are directed into vacuum chamber 214.

The laser device 220 can be a laser diode, such as a DBR laser. An electro-optic modulator 222 is configured to receive a pulsed laser beam 221 emitted by laser device 220, with laser beam 221 having a first frequency $f_0$. The laser beam 221 can be passed through a first collimator 224 prior to entering electro-optic modulator 222. The electro-optic modulator 222 outputs a first optical signal corresponding to the pulsed laser beam at the first frequency ($f_0$) and a second optical signal having a second frequency ($f_0 + f_{RF}$). The first and second optical signals are sent through a second collimator 226 to vacuum cell 210. The first and second collimators 224, 226 can be single lens or multi-lens collimators.

The movable piezo mirror structure 230 is located outside of vacuum cell 210 on an opposite side from second collimator 226. In one embodiment, piezo mirror structure 220 includes a piezoelectric element 232, a mirror element 234 on the piezoelectric element 232, and a quarter-waveplate 236 on mirror element 234. A piezo controller 238 is operatively coupled to piezoelectric element 232 and provides a sawtooth displacement with a velocity $v_0$. This in turn causes the mirror element 232 to have a corresponding velocity $v_0$ yielding a Doppler shift $f_D = f_0 v_0/c$.

The atomic interferometric accelerometer 200 also includes a set of beam splitters or Faraday isolators, which direct the emitted laser beam and the retro-reflected laser beam to a photodetector 240. In one embodiment a first beam splitter 242 samples beam 221 emitted from laser device 220 and directs the sampled emitted beam to a mirror 244. A second beam splitter 246 in the path of the output from electro-optic modulator 222 samples the beam reflected from the piezo mirror structure 230 and directs the sampled reflected beam to a third beam splitter 248, which also receives the sampled emitted beam from mirror 244. The beam splitter 248 directs the sampled emitted and reflected beams to photodetector 240.

A beat note detected by photodetector 240 is used to track the velocity of piezoelectric element 232. This can be implemented by beating one of the retro-reflected frequencies with one of the incident frequencies, so that the beat note encodes information about the piezo velocity. A filtering scheme can be employed if needed to select a desired beat note. The beat note produces an error signal that is sent in a feedback loop 250 from photodetector 240 to piezo controller 238 to stabilize the travel velocity of piezoelectric element 232, which in turn maintains a stable mirror velocity. The beat note can be optionally combined with a reference RF signal to produce an error signal that is sent in feedback loop 250 to piezo controller 238.

Figure 3:
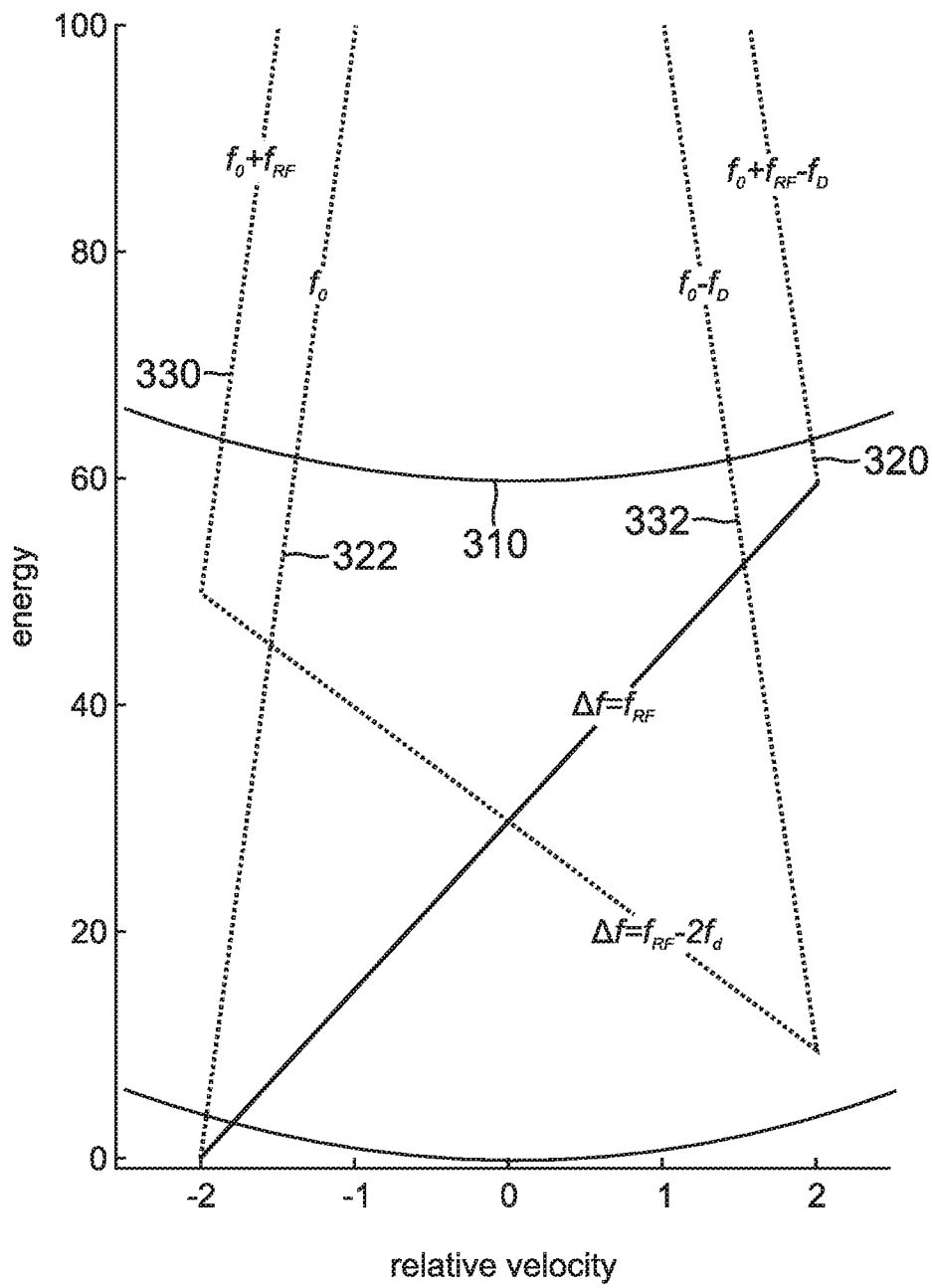
FIG. 3 is a graph of laser energy with respect to relative velocity of atoms, which shows how the laser energy difference needs to bridge the hyperfine gap between atomic energy levels in an atomic interferometric accelerometer.

FIG. 3 is a graph of laser energy with respect to relative velocity of atoms, which shows how the laser energy difference needs to bridge the hyperfine gap between atomic energy levels in an atomic interferometric accelerometer. The curve 310 indicates the energy spread due to atom velocity distribution. As indicated in FIG. 3, a laser beam pair comprised of a Doppler shifted beam 320 ($f_0+f_{RF}-f_D$) and an unshifted beam 322 ($f_0$) successfully bridges the hyperfine gap ($\Delta f=f_{RF}$). The other laser beam pair comprised of an unshifted beam 330 ($f_0+f_{RF}$) and a Doppler shifted beam 332 ($f_0-f_D$) has an energy difference that is too small to bridge the hyperfine gap ($\Delta f-f_{RF}-2f_d$), missing by an amount ($2f_d$) that must be greater than the energy spread due to atom temperature.

Example Embodiments

Example 1 includes an atomic interferometric accelerometer comprising: a laser device configured to emit a pulsed laser beam at a first frequency; an electro-optic modulator in optical communication with the laser device and configured to receive the pulsed laser beam at the first frequency, the electro-optic modulator configured to output a first optical signal corresponding to the pulsed laser beam at the first frequency and a second optical signal having a second frequency different from the first frequency; a vacuum cell in optical communication with the electro-optic modulator, the vacuum cell comprising a plurality of optically transparent sides that enclose a vacuum chamber in which laser cooled atoms reside, the vacuum cell configured to receive the first and second optical signals such that the first and second optical signals propagate in a direction that passes through the laser cooled atoms; and a piezo mirror structure in optical communication with the vacuum cell and configured to retro-reflect the first and second optical signals back through the laser cooled atoms in a counter-propagating direction; wherein the piezo mirror structure is driven with substantially constant velocity during each individual laser beam pulse, thereby imparting a Doppler shift to the retro-reflected first and second optical signals to create two non-symmetric counter-propagating lightwave pairs, wherein one of the lightwave pairs supports interferometry while the other of the lightwave pairs is non-resonant.

Example 2 includes the atomic interferometric accelerometer of Example 1, wherein the laser device comprises a laser diode.

Example 3 includes the atomic interferometric accelerometer of any of Examples 1-2, further comprising a first collimator located in a first optical path between the laser device and the electro-optic modulator, wherein the pulsed laser beam is passed through the first collimator prior to being received by the electro-optic modulator.

Example 4 includes the atomic interferometric accelerometer of Example 3, further comprising a second collimator located in a second optical path between the electro-optic modulator and the vacuum cell, wherein the first and second optical signals pass through the second collimator prior to being received by the vacuum cell.

Example 5 includes the atomic interferometric accelerometer of Example 4, wherein the first and second collimators each comprise a single lens collimator or a multi-lens collimator.

Example 6 includes the atomic interferometric accelerometer of any of Examples 1-5, wherein the laser cooled atoms comprise alkali atoms selected from the group consisting of rubidium, and cesium.

Example 7 includes the atomic interferometric accelerometer of any of Examples 1-6, wherein the piezo mirror structure is located outside of the vacuum cell on an opposite side from the second collimator.

Example 8 includes the atomic interferometric accelerometer of any of Examples 1-7, wherein the piezo mirror structure comprises: a piezoelectric element; a mirror element coupled to the piezoelectric element; and a quarter-waveplate coupled to the mirror element.

Example 9 includes the atomic interferometric accelerometer of Example 8, further comprising a piezo controller operatively coupled to the piezoelectric element, the piezo controller imparting a sawtooth displacement at a first velocity to the piezoelectric element.

Example 10 includes the atomic interferometric accelerometer of Example 9, further comprising a photodetector configured to receive a portion of the retro-reflected first and second optical signals and detect a beat note.

Example 11 includes the atomic interferometric accelerometer of Example 10, wherein a retro-reflected frequency is beat with an incident frequency so that the beat note encodes information about the velocity of the piezoelectric element.

Example 12 includes the atomic interferometric accelerometer of any of Examples 10-11, wherein the beat note detected by the photodetector is used to track the velocity of the piezoelectric element.

Example 13 includes the atomic interferometric accelerometer of any of Examples 10-12, wherein the beat note produces an error signal that is sent in a feedback loop from the photodetector to the piezo controller to stabilize the velocity of the piezoelectric element.

Example 14 includes the atomic interferometric accelerometer of any of Examples 10-13, wherein the beat note is combined with a reference RF signal to produce an error signal that is sent in a feedback loop from the photodetector to the piezo controller to stabilize the velocity of the piezoelectric element.

Example 15 includes the atomic interferometric accelerometer of any of Examples 10-14, further comprising a set of beam splitters or Faraday isolators, which direct the emitted pulsed laser beam and the retro-reflected first and second optical signals to the photodetector.

Example 16 includes an atomic interferometric accelerometer comprising: a laser device configured to emit a pulsed laser beam at a first frequency; an electro-optic modulator in optical communication with the laser device and configured to receive the pulsed laser beam at the first frequency, the electro-optic modulator configured to output a first optical signal corresponding to the pulsed laser beam at the first frequency and a second optical signal have a second frequency different from the first frequency; a vacuum cell in optical communication with the electro-optic modulator, the vacuum cell comprising a plurality of optically transparent sides that enclose a vacuum chamber in which laser cooled atoms reside, the vacuum cell configured to receive the first and second optical signals such that the first and second optical signals propagate in a direction that passes through the laser cooled atoms; a piezo mirror structure in optical communication with the vacuum cell and configured to retro-reflect the first and second optical signals back through the laser cooled atoms in a counter-propagating direction; a piezo controller operatively coupled to the piezo mirror structure, the piezo controller imparting a periodic displacement at a first velocity to the piezo mirror structure; and a photodetector configured to receive a portion of the retro-reflected first and second optical signals and detect a beat note; wherein the beat note produces an error signal that is sent in a feedback loop from the photodetector to the piezo controller to stabilize the velocity of the piezo mirror structure; wherein the piezo mirror structure is driven with substantially constant velocity during each individual laser beam pulse, thereby imparting a Doppler shift to the retro-reflected first and second optical signals to create two non-symmetric counter-propagating lightwave pairs, wherein one of the lightwave pairs supports interferometry while the other of the lightwave pairs is non-resonant.

Example 17 includes the atomic interferometric accelerometer of Example 16, wherein the laser device comprises a distributed Bragg reflector laser.

Example 18 includes the atomic interferometric accelerometer of any of Examples 16-17, wherein the piezo mirror structure comprises: a piezoelectric element; a mirror element coupled to the piezoelectric element; and a quarter-waveplate coupled to the mirror element.

Example 19 includes the atomic interferometric accelerometer of any of Examples 16-18, wherein the piezo mirror structure is located outside of the vacuum cell on an opposite side from the electro-optic modulator.

Example 20 includes the atomic interferometric accelerometer of any of Examples 16-19, further comprising a set of beam splitters or Faraday isolators, which direct the emitted pulsed laser beam and the retro-reflected first and second optical signals to the photodetector.

The present invention may be embodied in other specific forms without departing from its essential characteristics. The described embodiments are to be considered in all respects only as illustrative and not restrictive. The scope of the invention is therefore indicated by the appended claims rather than by the foregoing description. All changes that come within the meaning and range of equivalency of the claims are to be embraced within their scope.

What is claimed is:

1. An atomic interferometric accelerometer, comprising:
   a laser device configured to emit a pulsed laser beam at a first frequency;
   an electro-optic modulator in optical communication with the laser device and configured to receive the pulsed laser beam at the first frequency, the electro-optic modulator configured to output a first optical signal corresponding to the pulsed laser beam at the first frequency and a second optical signal having a second frequency different from the first frequency;
   a vacuum cell in optical communication with the electro-optic modulator, the vacuum cell comprising a plurality of optically transparent sides that enclose a vacuum chamber in which laser cooled atoms reside, the vacuum cell configured to receive the first and second optical signals such that the first and second optical signals propagate in a direction that passes through the laser cooled atoms; and
   a piezo mirror structure in optical communication with the vacuum cell and configured to retro-reflect the first and second optical signals back through the laser cooled atoms in a counter-propagating direction;
   wherein the piezo mirror structure is driven with substantially constant velocity during each individual laser beam pulse, thereby imparting a Doppler shift to the retro-reflected first and second optical signals to create two non-symmetric counter-propagating lightwave pairs, wherein one of the lightwave pairs supports interferometry while the other of the lightwave pairs is non-resonant.

2. The atomic interferometric accelerometer of claim 1, wherein the laser device comprises a laser diode.

3. The atomic interferometric accelerometer of claim 1, further comprising a first collimator located in a first optical path between the laser device and the electro-optic modulator, wherein the pulsed laser beam is passed through the first collimator prior to being received by the electro-optic modulator.

4. The atomic interferometric accelerometer of claim 3, further comprising a second collimator located in a second optical path between the electro-optic modulator and the vacuum cell, wherein the first and second optical signals pass through the second collimator prior to being received by the vacuum cell.

5. The atomic interferometric accelerometer of claim 4, wherein the first and second collimators each comprise a single lens collimator or a multi-lens collimator.

6. The atomic interferometric accelerometer of claim 1, wherein the laser cooled atoms comprise alkali atoms selected from the group consisting of rubidium, and cesium.

7. The atomic interferometric accelerometer of claim 4, wherein the piezo mirror structure is located outside of the vacuum cell on an opposite side from the second collimator.

8. The atomic interferometric accelerometer of claim 1, wherein the piezo mirror structure comprises:
   a piezoelectric element;
   a mirror element coupled to the piezoelectric element; and
   a quarter-waveplate coupled to the mirror element.

9. The atomic interferometric accelerometer of claim 8, further comprising a piezo controller operatively coupled to the piezoelectric element, the piezo controller imparting a sawtooth displacement at a first velocity to the piezoelectric element.

10. The atomic interferometric accelerometer of claim 9, further comprising a photodetector configured to receive a portion of the retro-reflected first and second optical signals and detect a beat note.

11. The atomic interferometric accelerometer of claim 10, wherein a retro-reflected frequency is beat with an incident frequency so that the beat note encodes information about the velocity of the piezoelectric element.

12. The atomic interferometric accelerometer of claim 11, wherein the beat note detected by the photodetector is used to track the velocity of the piezoelectric element.

13. The atomic interferometric accelerometer of claim 10, wherein the beat note produces an error signal that is sent in a feedback loop from the photodetector to the piezo controller to stabilize the velocity of the piezoelectric element.

14. The atomic interferometric accelerometer of claim 10, wherein the beat note is combined with a reference RF signal to produce an error signal that is sent in a feedback loop from the photodetector to the piezo controller to stabilize the velocity of the piezoelectric element.

15. The atomic interferometric accelerometer of claim 10, further comprising a set of beam splitters or Faraday isolators, which direct the emitted pulsed laser beam and the retro-reflected first and second optical signals to the photodetector.

16. An atomic interferometric accelerometer, comprising:
a laser device configured to emit a pulsed laser beam at a first frequency;
an electro-optic modulator in optical communication with the laser device and configured to receive the pulsed laser beam at the first frequency, the electro-optic modulator configured to output a first optical signal corresponding to the pulsed laser beam at the first frequency and a second optical signal have a second frequency different from the first frequency;
a vacuum cell in optical communication with the electro-optic modulator, the vacuum cell comprising a plurality of optically transparent sides that enclose a vacuum chamber in which laser cooled atoms reside, the vacuum cell configured to receive the first and second optical signals such that the first and second optical signals propagate in a direction that passes through the laser cooled atoms;
a piezo mirror structure in optical communication with the vacuum cell and configured to retro-reflect the first and second optical signals back through the laser cooled atoms in a counter-propagating direction;
a piezo controller operatively coupled to the piezo mirror structure, the piezo controller imparting a periodic displacement at a first velocity to the piezo mirror structure; and
a photodetector configured to receive a portion of the retro-reflected first and second optical signals and detect a beat note;
wherein the beat note produces an error signal that is sent in a feedback loop from the photodetector to the piezo controller to stabilize the velocity of the piezo mirror structure;
wherein the piezo mirror structure is driven with substantially constant velocity during each individual laser beam pulse, thereby imparting a Doppler shift to the retro-reflected first and second optical signals to create two non-symmetric counter-propagating lightwave pairs, wherein one of the lightwave pairs supports interferometry while the other of the lightwave pairs is non-resonant.

17. The atomic interferometric accelerometer of claim 16, wherein the laser device comprises a distributed Bragg reflector laser.

18. The atomic interferometric accelerometer of claim 16, wherein the piezo mirror structure comprises:
a piezoelectric element;
a mirror element coupled to the piezoelectric element; and
a quarter-waveplate coupled to the mirror element.

19. The atomic interferometric accelerometer of claim 18, wherein the piezo mirror structure is located outside of the vacuum cell on an opposite side from the electro-optic modulator.

20. The atomic interferometric accelerometer of claim 18, further comprising a set of beam splitters or Faraday isolators, which direct the emitted pulsed laser beam and the retro-reflected first and second optical signals to the photodetector.

* * * * *